United States Patent [19]

Suhr

[11] 4,173,639
[45] Nov. 6, 1979

[54] 1-BENZOYL-3-(ALKOXY- OR ALKYLTHIOPYRIDINYL)UREAS

[75] Inventor: Robert G. Suhr, Greenfield, Ind.
[73] Assignee: Eli Lilly and Company, Indianapolis, Ind.
[21] Appl. No.: 938,722
[22] Filed: Aug. 31, 1978
[51] Int. Cl.$^2$ ............... C07D 213/76; A01N 9/22
[52] U.S. Cl. .................................. 424/263; 546/292
[58] Field of Search .................. 546/292; 424/263

[56] References Cited

U.S. PATENT DOCUMENTS

| | | | |
|---|---|---|---|
| 3,748,356 | 7/1973 | Wellings et al. | 260/553 E |
| 4,083,977 | 4/1978 | Miesel | 424/250 |
| 4,092,421 | 5/1978 | Wade et al. | 424/266 |

OTHER PUBLICATIONS

Wellings et al., J. Agr. Food Chem., vol. 21, No. 6, pp. 993–998 (1973).
Hajjar et al., Science, vol. 200, pp. 1499–1500 (1978).
DeMilo et al., J. Agr. Food Chem., vol. 28, No. 1, pp. 164–166, 1978.

*Primary Examiner*—Alan L. Rotman
*Attorney, Agent, or Firm*—Kathleen R. S. Page; Arthur R. Whale

[57] ABSTRACT

The present invention is directed to 1-benzoyl-3-(alkoxy- or alkylthiopyridinyl)urea compounds useful as insecticides.

21 Claims, No Drawings

1-BENZOYL-3-(ALKOXY- OR ALKYLTHIOPYRIDINYL)UREAS

SUMMARY OF THE INVENTION

More particularly, the present invention is directed to novel compounds of the formula

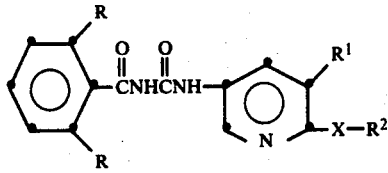

wherein each R is independently chloro, fluoro, methyl, or methoxy; $R^1$ is H, Cl, $CH_3$, or $C_2H_5$; X is O, S,

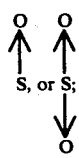

and $R^2$ is alkyl of $C_1$–$C_5$, alkenyl of $C_3$–$C_5$ containing no $\alpha,\beta$-unsaturation, mono- or dibromo-$C_1$–$C_5$ alkyl, chloroalkyl of $C_1$–$C_5$, fluoroalkyl of $C_1$–$C_5$, cycloalkyl of $C_4$–$C_6$, or alkoxyalkyl of a total of $C_2$–$C_5$; and the acid addition salts thereof.

The present invention is also directed to methods and compositions comprising the above compounds as insecticides.

DETAILED DESCRIPTION OF THE INVENTION

For the purposes of the present application, the compounds of this invention are named as substituted ureas, with numbering as follows:

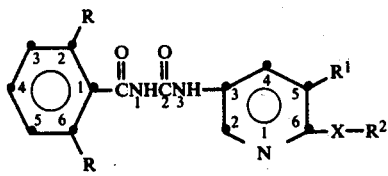

Thus, the compounds are named as 1-(2,6-disubstituted benzoyl)-3-(5-$R^1$-6-X-$R^2$-3-pyridinyl)ureas, or acid addition salts thereof.

In the foregoing definition, fluoralkyl of $C_1$–$C_5$ refers to $C_1$–$C_5$ alkyl bearing from one fluorine to as many fluorine as the alkyl permits, i.e., perfluorinated. Representative perfluoroalkyl radicals include trifluoromethyl, 2,2,2-trifluoroethyl, 1-methyl-2,2,3,3,3-pentafluoropropyl, 2-methyl-1,1,1,3,3,3-hexafluoro-2-propyl, 2,2,3,3,4,4,4-heptafluorobutyl, 3,3,4,4,5,5,5-heptafluoro-2-pentyl, 2,2,-3,3,4,4,5,5-octafluoropentyl, 3,3,4,4,4-pentafluoro-2-butyl, 2,2,3,3,3-pentafluoropropyl, perfluoro-tert-butyl, 2,2,3,3-tetrafluoropropyl, and 2-(trifluoromethyl)-2-propyl. Similarly, chloroalkyl of $C_1$–$C_5$ refers to $C_1$–$C_5$ alkyl bearing from one chlorine to as many chlorine as the alkyl permits, i.e., perchlorinated. Representative radicals include chloromethyl, dichloromethyl, trichloromethyl, 2,2,2-trichloroethyl, 1,1,1-trichloro-2-propyl, and 1,1,1-trichloro-2-methyl-2-propyl; generally, mono-, di-, or trichloro substituted radicals are preferred.

The compounds of the present invention are readily prepared by the reaction of a benzoyl isocyanate of the formula

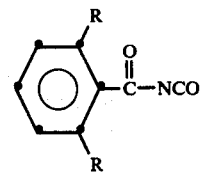

with a 3-aminopyridine of the formula

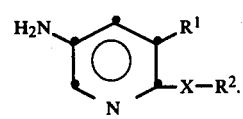

The reaction is a known type of reaction, cf. U.S. Pat. No. 3,748,356. The reaction is conveniently conducted in an organic solvent such as ethyl acetate, at room temperature, and with equimolar amounts of the reactants.

The acid addition salts are prepared by reacting a product with the desired acid in conventional procedures. Acids having a pKa of 3 or lower are preferred, and generally the mineral acids are preferred.

The benzoyl isocyanates which serve as starting materials are prepared by the reaction of the corresponding benzamide with oxalyl chloride, by the method of Speziale et al., J. Org. Chem. 27, 3742 (1962).

The 3-aminopyridine starting materials are prepared from the corresponding halonitropyridines

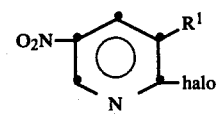

The halonitropyridine is first condensed with an alcohol or thiol of the formula $HX-R^2$ and the resulting compound

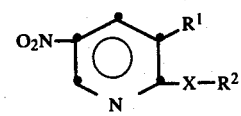

is then reduced. The condensation is conducted in a solvent such as DMF, DMSO, THF, etc., and in the presence of a base, such as triethylamine, KOH, LiOH, NaH, etc., to serve as a hydrogen halide acceptor. Preferred conditions are equimolar amounts of the reactants in DMF, at room temperature, and with lithium hydroxide as base. The reduction can be carried out in any of various prior art procedures, including $SnCl_2$/HCl, catalytic hydrogenation, and powdered iron with ammonium chloride. Preferred conditions are powdered iron and ammonium chloride.

For final products wherein

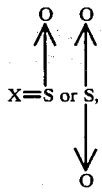

it is preferred to oxidize the sulfur of the 6-SR²-3-aminopyridine starting material and employ it in the reaction with the benzoyl isocyanate, to obtain the product wherein

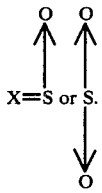

Many of the halonitropyridines are commercially available and all are prepared in known procedures. See Acharya et al., *Chem. Abst.* 58, 5623c (1963); Batkowski, *Chem. Abst.* 70, 106327x (1969); and Hawkins et al., *J. Org. Chem.* 14, 328 (1949). The synthesis of these and numerous other pyridine compounds has been well reviewed in *Pyridine and Its Derivatives*, ed. by Klingsberg, especially Parts 2 and 3 (Interscience Publishers, New York, N.Y. 1961 and 1962).

Most of the alkanols and cycloalkanols, and many of the alkanethiols and cycloalkanethiols are also commercially available. All can be prepared in prior art procedures. A convenient procedure for converting an alcohol to a alkanethiol, or a cycloalkanol to a cycloalkanethiol, is that of Newman et al., J. Org. Chem. 31, 3980 (1966).

Preferred compounds of the present invention are
(1) those wherein R is in both occurrences the same moiety and is either chloro, fluoro, or methoxy; and
(2) those wherein R² is a branched $C_3$–$C_5$ alkyl, especially tert-butyl, and wherein R² is cyclohexyl.

The following examples illustrate the synthesis of the compounds of the present invention.

EXAMPLE 1

2-(2,2,2-Trifluoroethoxy)-5-Nitropyridine

2-Chloro-5-nitropyridine (9.5 grams), 2,2,2-trifluoroethanol (6.0 grams), and lithium hydroxide (4.0 grams) were mixed in 50 ml. of DMSO and stirred overnight (about 18 hours) at room temperature. The reaction mixture was then poured into water and the product was separated by filtration. It was crystallized from ethyl acetate-hexanes, yield 5.0 grams, m.p., 35°–37° C.

Calc. for $C_7H_5F_3N_2O_3$: C, 37.85; H, 2.27; N, 12.61. Found: C, 37.58; H, 2.25; N, 12.79.

EXAMPLE 2

2-(2,2,2-Trifluoroethoxy)-3-Aminopyridine 2-(2,2,2-Trifluoroethoxy)-5-nitropyridine (5.0 grams), powdered iron (15 grams), and ammonium chloride (25 grams) were refluxed in 3A ethanol until TLC detected no starting material (about 4 hours). The reaction mixture was filtered, washed with water, and solvents removed, yielding 1.0 gram of the product as a thin brownish liquid. NMR confirmed the identity of the product.

EXAMPLE 3

2-tert-Butoxy-5-Nitropyridine

To 50 ml. of tert-butanol, there was added potassium tert-butoxide (0.06 mole) and 2-chloro-5-nitropyridine (0.05 mole). A white solid precipitated. The reaction mixture was heated to about 60° for 4 hours. Excess ammonium chloride was added to neutralize excess potassium tert-butoxide. Solvent was removed by evaporation, and the residue was taken up in chloroform, separated, washed with water, dried over magnesium sulfate, and chromatographed on silica gel with a 50:50 mixture of ethyl acetate:toluene. The structure was confirmed by NMR spectroscopy.

EXAMPLE 4

2-Cyclohexylthio-5-Aminopyridine

2-Cyclohexylthio-5-nitropyridine (13.4 grams) was added to a suspension of 50 grams of ammonium chloride and 20 grams of powdered iron in a mixture of 220 ml. of ethyl acetate and 30 ml. of water. The reaction mixture was refluxed for 6 hours. TLC indicated some starting material remained. Additional powdered iron (10 grams) was added and the reaction mixture refluxed for another 2 hours. TLC indicated no starting material remaining. The reaction mixture was filtered, taken up in chloroform, washed with water, dried, and evaporated. The main product residue was crystallized from ethyl acetate-hexanes, 8.4 grams of tan crystals; a second crop was crystalled from chloroform-hexanes with charcoal, 0.8 gram. The second crop was analyzed as follows:

Calc. for $C_{11}H_{16}N_2S$: C, 63.46; H, 7.69; N, 13.46. Found: C, 63.27; H, 7.44; N, 12.23.

EXAMPLE 5

2-Cyclohexylsulfonyl-5-Nitropyridine

2-Cyclohexylthio-5-nitropyridine (3.5 grams) was dissolved in methylene chloride and m-chloroperbenzoic acid (7.0 grams) was added portionwise at room temperature. The reaction was slightly exothermic. The reaction mixture was stirred at room temperature for 2 hours after the addition was completed. The reaction mixture was then washed with saturated sodium bicarbonate solution and water, solvent was removed, and the residue was passed over a silica gel column with ethyl acetate. The major spot ($R_f \approx 0.5$) was isolated and crystallized from ethyl acetate-hexanes, m.p., 182°–185° C.

Calc. for $C_{11}H_{16}N_2O_2S$: C, 54.98; H, 6.71; N, 11.66. Found: C, 54.78; H, 6.43; N, 11.63.

EXAMPLE 6

2,6-Dichlorobenzoyl Isocyanate

A one-liter flask was purged with nitrogen while dry 2,6-dichlorobenzamide (125 grams, 0.64 mole) and dry toluene (300 ml.) were added. The nitrogen purge was continued as oxalyl chloride (100 grams, 0.79 mole) was added over a 15-minute period, with stirring. The reaction mixture was then heated to 55° C. and stirred overnight (about 18 hours) at 55° C.

The reaction mixture was then heated to reflux (111° C.) and refluxed for 2 hours. Solvent was removed under vacuum and the product distilled off at 134°–135° C. flask temperature and 131°–132° C. vapor temperature, at 13 mm. vacuum, yield 127.5 grams (92.5%).

Calc. for $C_{19}H_{12}Cl_3N_3O_2S$: C, 50.41; H, 2.67; N, 9.28. Found: C, 50.54; H, 2.97; N, 9.45.

EXAMPLE 7

1-(2,6-Dimethoxybenzoyl)-3-(6-Cyclohexylsulfonyl-3-Pyridinyl)Urea

2-Cyclohexylsulfonyl-5-aminopyridine (1.0 gram) and 2,6-dimethoxybenzoyl isocyanate (0.9 gram) were mixed in 50 ml. of DMF and stirred at room temperature overnight (about 18 hours). The reaction mixture was then poured into water and filtered to separate the product. It was crystallized from ethyl acetate-hexanes, yield 0.5 gram, m.p., 123°–125° C.

Calc. for $C_{21}H_{25}N_3O_6S$: C, 56.36; H, 5.63; N, 9.39. Found: C, 56.10; H, 5.51; N, 9.58.

EXAMPLE 8

1-(2,6-Dichlorobenzoyl)-3-(6-(2,2,2-Trifluoroethoxy)-3-Pyridinyl)Urea 2-(2,2,2-Trifluoroethoxy)-5-aminopyridine (0.5 gram) and 2,6-dichlorobenzoyl isocyanate (0.5 gram) were mixed in ethyl acetate, and the reaction mixture stirred overnight (about 18 hours) at room temperature. Solvent was removed by evaporation and the product residue crystallized from ethyl acetate-hexanes, yield 0.6 gram, m.p., 146°–148° C.

Calc. for $C_{15}H_{10}Cl_2F_3N_3O_3$: C, 44.14; H, 2.47; N, 10.30. Found: C, 44.36; H, 2.54; N, 10.03.

EXAMPLES 9-24

Other representative compounds of the present invention include the following.

| Example No. | Compound Name | m.p. or other confirmatory data |
|---|---|---|
| 9 | 1-(2,6-dimethoxybenzoyl)-3-(6-methoxy-3-pyridinyl)urea | m.p., 204–207° C. |
| 10 | 1-(2,6-dichlorobenzoyl)-3-(6-methoxy-3-pyridinyl)urea | m.p., 188–191° C. |
| 11 | 1-(2,6-dichlorobenzoyl)-3-(6-tert-butoxy-3-pyridinyl)urea | Calc. for $C_{17}H_{17}N_3O_3$: C, 53.42; H, 4.48; N, 10.99. Found: C, 53.20; H, 4.51; N, 10.94. |
| 12 | 1-(2,6-dichlorobenzoyl)-3-(6-n-butoxy-3-pyridinyl)urea | Calc. for $C_{17}H_{17}Cl_2N_3O_2$: C, 53.42; H, 4.48; N, 10.99. Found: C, 53.59; H, 4.30; N, 11.05. |
| 13 | 1-(2,6-dichlorobenzoyl)-3-(6-n-pentylthio-3-pyridinyl)urea | Calc. for $C_{18}H_{19}N_3O_2S$: C, 52.43; H, 4.64; N, 10.19. Found: C, 52.19; H, 4.66; N, 10.26. |
| 14 | 1-(2,6-dimethoxybenzoyl)-3-(6-tert-butoxy-3-pyridinyl)urea | m.p., 245–248° C. |
| 15 | 1-(2,6-dimethoxybenzoyl)-3-(6-n-butoxy-3-pyridinyl)urea | m.p., 134–137° C. |
| 16 | 1-(2,6-dimethoxybenzoyl)-3-(6-n-pentyloxy-3-pyridinyl)urea | Calc. for $C_{20}H_{25}N_3O_4S$: C, 59.53; H, 6.25; N, 10.41. Found: C, 59.31; H, 6.15; N, 10.16. |
| 17 | 1-(2,6-dichlorobenzoyl)-3-(6-(2-methoxyethoxy)-3-pyridinyl)urea | Calc. for $C_{16}H_{15}Cl_2N_3O_4$: C, 50.02; H, 3.94; N, 10.94. Found: C, 50.24; H, 3.73; N, 11.06. |
| 18 | 1-(2,6-dimethoxybenzoyl)-3-(6-(2-methoxyethoxy)-3-pyridinyl)urea | m.p., 157–160° C. |
| 19 | 1-(2,6-dichlorobenzoyl)-3-(6-tert-butylthio-3-pyridinyl)urea | Calc. for $C_{17}H_{17}Cl_2N_3O_2S$: C, 51.26; H, 4.30; N, 10.55. Found: C, 51.26; H, 4.30; N, 10.68. |
| 20 | 1-(2,6-dichlorobenzoyl)-3-(6-cyclohexlthio-3-pyridinyl)urea | calc. for $C_{19}H_{19}ClN_3O_2$: C, 53.77; H, 4.48; N, 9.91. Found: C, 53.44; H, 4.31; N, 9.96. |
| 21 | 1-(2,6-dimethoxybenzoyl)-3-(6-tert-butylthio-3-pyridinyl)urea | Crop No. 1, m.p., 220–222° C. Crop No. 2, m.p., 205–215° C. Calc. for $C_{19}H_{23}N_3O_4S$: C, 58.59; H, 5.95; N, 10.79. Crop No. 1, Found: C, 58.35; H, 5.74; N, 10.80. Crop No. 2, Found: C, 58.80; H, 5.74; N, 11.01. |
| 22 | 1-(2,6-dimethoxybenzoyl)-3-(6-cyclohexyl-thio-3-pyridinyl)urea | Calc. for $C_{21}H_{25}N_3O_4Cl$: C, 60.70; H, 6.06; N, 10.11. Found: C, 60.69; H, 5.86; N, 9.90. |
| 23 | 1-(2,6-dimethoxybenzoyl)-3-(6-(2,2,2-tri-)fluoroethoxy)-3-pyridinyl)urea | Calc. for $C_{17}H_{16}F_3N_3O_5$: C, 51.13; H, 4.04; N, 10.52. Found: C, 51.36; H, 4.04; N, 10.22. |
| 24 | 1-(2,6-dichlorobenzoyl)-3-(6-cyclohexylsulfonyl-3-pyridinyl)urea | m.p., 182–185° C. |

The compounds of the present invention are useful for the control of insects of various orders, including Coleoptera such as Mexican bean beetle, boll weevil, corn rootworms, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, white grubs; Diptera, such as house fly, yellow fever mosquito, stable fly, horn fly, blowfly, cabbage maggot, carrot rust fly; Lepidoptera, such as southern armyworm, codling moth, cutworm, clothes moth, Indian meal moth, leaf rollers, corn earworm, European corn borer, cabbage worm, cabbage looper, cotton bollworm, bagworm, eastern tent caterpillar, sod webworm, fall armyworm; and Orthoptera, such as German cockroach and American cockroach.

It is believed that the present compounds act by interfering with the mechanism of metamorphosis which occurs in insects, causing the death of the insects. It is also believed that ingestion by the insects is necessary to invoke this mechanism. While the death of any given insect may be delayed until that insect reaches some stage of metamorphosis, the net result of this activity is the control and suppression of insects.

Therefore, in another embodiment, the present invention is directed to a method of suppressing insects which comprises applying to a locus of the insects an effective amount of a compound of the present invention. The locus can be any environment inhabited by insects to be controlled, such as soil, air, water, foods, vegetation, manure, inert objects, stored matter such as grain, and the like.

Preferably the compounds of the present invention are supplied in a formulation, for ease of application. The compounds can be formulated with various adjuvants, including water, organic liquids, surface-active agents, inert solids, and the like. Suitable surface-active include anionic agents, such as sodium lauryl sulfate, sodium dodecylbenzenesulfonate, and the like; and nonionic agents, such as polyethylene glycol p-nonylphenyl ether. Mixtures are often desirably employed. The formulation can take the form of a liquid, dust, granule, aerosol, etc. The formulation can be concentrated, as in a slow-release formulation or as in a formulation to be diluted with water before application to the locus of insects. Many methods of formulation are known in the art and can be employed to implement the present invention.

The concentration of active agent in the formulation is not critical, inasmuch as an effective concentration will vary with the nature of the locus to be treated, the severity of insect infestation, the susceptibility of the particular insects involved, etc. In general, concentrations ranging from about 1 to 1000 ppm give good results. As exemplified by Table 2, below, lesser concentrations of from about 1 to about 100 ppm have given good control of Mexican bean beetle.

The insecticidal activity of the present compounds was determined by testing the efficacy of formulations of the compounds against Mexican bean beetle larvae (*Epilachna varivestis*), and against southern armyworm larvae (*Spodoptera eridania*). These insects are members of the Coleoptera and Lepidoptera orders of insects, respectively. The formulations were applied to the foliage of plants and the larvae were subsequently permitted to feed on the foliage. The compounds were tested in a plurality of concentrations, from a concentration of about 1000 ppm. to about 1 ppm.

Each compound to be tested was formulated by dissolving 10 mg. of the compound in 1 ml. of a solvent made up with 23 grams of Toximul R and 13 grams of Toximul S per liter of 1:1 anhydrous ethanol and acetone. Each of Toximul R and Toximul S is a sulfonate/-nonionic blend produced by Stepan Chemical Company, Northfield, Ill. Water was then added to obtain 10 ml. of solution containing the compound in a concentration of 1000 parts per million. Alternatively, 11 mg. of compound was used, to make up 11 ml. of solution, of which 10 ml. was employed as a 1000 ppm. treating solution, and of which the remaining 1 ml. was diluted further with water to obtain a treating solution containing 100 ppm. of compound. Formulations of the compound at lesser concentrations were prepared in the same manner, using the same solvent.

Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×20 mm. plastic petri dishes. Five second-instar Mexican bean beetle larvae (*Epilachna varivestis*) and five second-and third-instar southern armyworm larvae (*Spodoptera eridania*) were placed in each of three dishes. The dishes were then placed in a room wherein the temperature and relative humidity were controlled at about 78° F. and about 51 percent, respectively, for a period of four days, at which time the first evaluation of the effects of the test compounds was made. After this evaluation, two fresh leaves from the original treated pots were placed in each dish. The dishes were again maintained in the temperature and humidity controlled room for an additional three days until the final seven-day evaluation was made.

Insecticidal effect was determined by counting the number of living larvae of each species, and applying the following rating code:

0 = all larvae alive
1 = half or more of the larvae alive
2 = less than half of the larvae alive
3 = all larvae dead The results of this test are set forth in Table 1, which follows. In the table, column 1 identifies the compounds by the number of the preparative example; column 2 lists the concentration of the test compound in the formulation; and columns 3 through 6 give the rating code at days 4 and 7 for the two insects against which the compounds were tested.

Table 1

| Example No. | Appln. Rate ppm | Insect Control | | | |
|---|---|---|---|---|---|
| | | Mexican Bean Beetle | | Southern Armyworm | |
| | | 4 days | 7 days | 4 days | 7 days |
| 7 | 1000 | 2 | 2 | 1 | 2 |
| | 100 | 1 | 2 | 2 | 2 |
| 9 | 1000 | 2 | 3 | 1 | 1 |
| | 100 | 2 | 3 | 0 | 0 |
| 10 | 1000 | 0 | 1 | 1 | 2 |
| | 100 | 0 | 0 | 0 | 0 |
| 11 | 1000 | 1 | 2 | 2 | 2 |
| | 100 | 0 | 1 | 1 | 1 |
| 12 | 1000 | 1 | 3 | 2 | 2 |
| | 100 | 1 | 3 | 1 | 2 |
| 13 | 1000 | 1 | 3 | 0 | 0 |
| | 100 | 0 | 3 | 0 | 0 |
| 14 | 1000 | 1 | 3 | 0 | 0 |
| | 100 | 0 | 3 | 0 | 0 |
| 15 | 1000 | 0 | 3 | 0 | 1 |
| | 100 | 0 | 3 | 0 | 1 |
| 16 | 1000 | 0 | 0 | 0 | 0 |
| | 100 | 0 | 0 | 0 | 0 |
| 17 | 1000 | 1 | 2 | 1 | 2 |
| | 100 | 0 | 1 | 0 | 1 |
| 18 | 1000 | 2 | 2 | 2 | 2 |
| | 100 | 1 | 2 | 1 | 2 |
| 19 | 1000 | 2 | 3 | 0 | 0 |
| | 100 | 2 | 3 | 0 | 0 |
| 20 | 1000 | 2 | 3 | 1 | 1 |
| | 100 | 2 | 3 | 0 | 0 |
| 21 | 1000 | 2 | 3 | 0 | 0 |
| | 100 | 2 | 3 | 0 | 0 |
| 22 | 1000 | 3 | 3 | 0 | 0 |
| | 100 | 3 | 3 | 0 | 0 |
| 23 | 1000 | 1 | 3 | 1 | 2 |
| | 100 | 2 | 3 | 0 | 1 |
| 24 | 1000 | 2 | 3 | 0 | 0 |
| | 100 | 1 | 2 | 0 | 0 |
| 8 | 1000 | 2 | 3 | 2 | 3 |
| | 100 | 1 | 3 | 3 | 3 |

In a further evaluation, the compounds of the present invention were retested in the same procedure described above but at lower concentrations. In the retest, percent control was determined by counting the number of living larvae per dish and using Abbott's formula [W. W. Abbott, "A Method of Computing the Effectiveness of an Insecticide", *J. Econ. Entomol.* 18, 265-7 (1925)]:

Percent Control =
$$\frac{\text{No. of survivors in control} - \text{No. of survivors in treatment} \times 100}{\text{No. survivors in control}}$$

The results are set forth in Table 2, which follows.

Table 2

| Example No. | Appln. Rate ppm | Insect Control (%) Mexican Bean Beetle 4 days | 7 days |
|---|---|---|---|
| | 10 | 0 | 0 |
| | 25 | 60 | 60 |
| | 50 | 33 | 80 |
| | 100 | 80 | 100 |
| | 10 | 0 | 7 |
| | 25 | 13 | 27 |
| | 50 | 53 | 47 |
| | 100 | 67 | 87 |
| | 10 | 67 | 93 |
| | 25 | 67 | 93 |
| | 50 | 86 | 100 |
| | 100 | 86 | 100 |
| | 1 | 67 | 80 |
| | 2.5 | 80 | 100 |
| | 5 | 86 | 93 |
| | 10 | 93 | 100 |
| | 0.1 | 0 | 0 |
| | 0.5 | 0 | 0 |
| | 1.0 | 7 | 53 |
| | 2.5 | 93 | 100 |
| | 10 | 93 | 100 |
| | 10 | 93 | 100 |
| | 25 | 93 | 100 |
| | 50 | 93 | 100 |
| | 100 | 93 | 100 |
| | 1.0 | 7 | 27 |
| | 2.5 | 86 | 93 |
| | 5 | 93 | 100 |
| | 10 | 100 | 100 |
| | 10 | 73 | 100 |
| | 25 | 80 | 100 |
| | 50 | 80 | 100 |
| | 100 | 80 | 100 |
| | 1.0 | 0 | 13 |
| | 2.5 | 27 | 40 |
| | 5. | 53 | 80 |
| | 10. | 93 | 93 |

I claim:
1. Compound of the formula

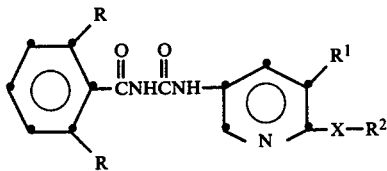

wherein each R is independently chloro, fluoro, methyl, or methoxy; $R^1$ is H, Cl, $CH_3$, or $C_2H_5$; X is O, S,

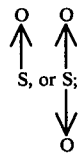

and $R^2$ is alkyl of $C_1$–$C_5$, alkenyl of $C_3$–$C_5$ containing no $\alpha,\beta$-unsaturation, mono- or dibromo-$C_1$–$C_5$ alkyl, chloroalkyl of $C_1$–$C_5$, fluoroalkyl of $C_1$–$C_5$, cycloalkyl of $C_4$–$C_6$, or alkoxyalkyl of a total of $C_2$–$C_5$; and the acid addition salts thereof.

2. The compound of claim 1 wherein R is in both cases the same moiety and is either chloro, fluoro, or methoxy; and wherein $R^2$ is a branched $C_3$–$C_5$ alkyl or cyclohexyl.

3. The compound of claim 2 which is 1-(2,6-dichlorobenzoyl)-3-(6-tert-butylthio-3-pyridinyl)urea.

4. The compound of claim 2 which is 1-(2,6-dimethoxybenzoyl)-3-(6-tert-butylthio-3-pyridinyl)urea.

5. The compound of claim 2 which is 1-(2,6-dichlorobenzoyl)-3-(6-cyclohexylthio-3-pyridinyl)urea.

6. The compound of claim 2 which is 1-(2,6-dimethoxybenzoyl)-3-(6-cyclohexylthio-3-pyridinyl)urea.

7. The compound of claim 2 which is 1-(2,6-difluorobenzoyl)-3-(6-cyclohexylthio-3-pyridinyl)urea.

8. Method of suppressing insects of an order selected from the group consisting of Coleoptera, Diptera, Lepidoptera, and Orthoptera, which comprises applying to the locus of the insects an effective amount of an active agent which is a compound of claim 1.

9. The method of claim 8 wherein, in the compound of claim 1, $R^2$ is a branched $C_3$–$C_5$ alkyl or cyclohexyl.

10. The method of claim 9 wherein the active agent is 1-(2,6-dichlorobenzoyl)-3-(6-tert-butylthio-3-pyridinyl)urea.

11. The method of claim 9 wherein the active agent is 1-(2,6-dimethoxybenzoyl)-3-(6-tert-butylthio-3-pyridinyl)urea.

12. The method of claim 9 wherein the active agent is 1-(2,6-dichlorobenzoyl)-3-(6-cyclohexylthio-3-pyridinyl)urea.

13. The method of claim 9 wherein the active agent is 1-(2,6-dimethoxybenzoyl)-3-(6-cyclohexylthio-3-pyridinyl)urea.

14. The method of claim 9 wherein the active agent is 1-(2,6-difluorobenzoyl)-3-(6-cyclohexylthio-3-pyridinyl)urea.

15. Composition comprising a surface active agent and an insecticidally effective amount of an active agent which is a compound of claim 1.

16. The composition of claim 15 wherein, in the compound of claim 1, $R^2$ is a branched $C_3$–$C_5$ alkyl or cyclohexyl.

17. The composition of claim 16 wherein the active agent is 1-(2,6-dichlorobenzoyl)-3-(6-tert-butylthio-3-pyridinyl)urea.

18. The composition of claim 16 wherein the active agent is 1-(2,6-dimethoxybenzoyl)-3-(6-tert-butylthio-3-pyridinyl)urea.

19. The composition of claim 16 wherein the active agent is 1-(2,6-dichlorobenzoyl)-3-(6-cyclohexylthio-3-pyridinyl)urea.

20. The composition of claim 16 wherein the active agent is 1-(2,6-dimethoxybenzoyl)-3-(6-cyclohexylthio-3-pyridinyl)urea.

21. The composition of claim 16 wherein the active agent is 1-(2,6-difluorobenzoyl)-3-(6-cyclohexylthio-3-pyridinyl)urea.

* * * * *